United States Patent [19]

Dugger

[11] Patent Number: 5,210,212
[45] Date of Patent: May 11, 1993

[54] PROCESS FOR 5-FLUORO-6-CHLOROOXINDOLE

[75] Inventor: Robert W. Dugger, Mystic, Conn.

[73] Assignee: Pfizer Inc, New York, N.Y.

[21] Appl. No.: 930,870

[22] Filed: Aug. 14, 1992

Related U.S. Application Data

[62] Division of Ser. No. 720,974, Jun. 25, 1991, Pat. No. 5,166,401.

[51] Int. Cl.$^5$ .......................................... C07D 209/34
[52] U.S. Cl. .................................................... 548/486
[58] Field of Search ........................................ 548/486

[56] References Cited

U.S. PATENT DOCUMENTS

| | | | |
|---|---|---|---|
| 4,160,032 | 7/1979 | Hardtmann | 424/274 |
| 4,207,341 | 6/1980 | Hübner et al. | 562/456 |
| 4,556,672 | 12/1985 | Kadin | 514/414 |
| 4,704,468 | 11/1987 | Zabunova et al. | 560/43 |
| 4,762,840 | 8/1988 | Rowlands et al. | 560/43 |
| 4,868,305 | 9/1989 | Cebula | 560/43 |

FOREIGN PATENT DOCUMENTS

| | | | |
|---|---|---|---|
| 4244 | 8/1966 | France | 562/456 |
| 1-125354 | 5/1989 | Japan | 562/456 |

OTHER PUBLICATIONS

Patrick et al., J. Org. Chem. 39:1758–1761 (1974).
Fidler et al., J. Org. Chem. 26:4014–4017 (1961).
Entwistle et al., Tetrahedron 34:213–215 (1978).
Hirai et al., Chem. Abstr. vol. 112, Entry 32154a (1988).
Jacques et al., C. R. Acad. Sc. Paris, 263 (4 Jul. 1966).

*Primary Examiner*—Robert W. Ramsuer
*Assistant Examiner*—Jacqueline Haley
*Attorney, Agent, or Firm*—Peter C. Richardson; Gregg C. Benson

[57] ABSTRACT

Process for the production of 5-fluoro-6-chloro- oxindole, (III), which is useful in the synthesis of certain analgesic and antiinflammatory agents, via two different synthetic pathways.

Compounds of formula (I) and (II) shown below

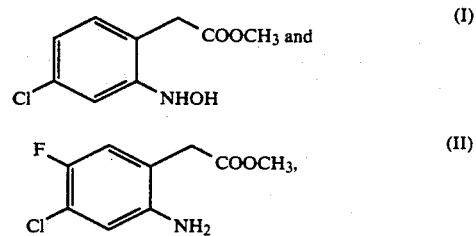

which are intermediates in the process of this invention.

5 Claims, No Drawings

PROCESS FOR 5-FLUORO-6-CHLOROOXINDOLE

This is a division of application Ser. No. 07/720,974, filed on Jun. 25, 1991, now U.S. Pat. No. 5,166,401.

BACKGROUND OF THE INVENTION

The present invention is directed to processes for the preparation of 5-fluoro-6-chlorooxindole (III). 5-Fluoro-6-chlorooxindole is particularly useful as an intermediate in the synthesis of certain analgesic and antiinflammatory agents having the formula

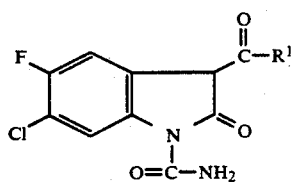

wherein $R^1$ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl, naphthyl, bicyclo[2.2.1]heptan-2-yl, bicyclo[2.2.1]-hept-5-en-2-yl and -(CH$_2$)$_n$-Q-R; wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and trifluoromethyl; n is zero, 1 or 2; Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydro-thiophene, tetrahydropyran, tetrahydrothiopyran, pyridine, pyrimidine, pyrazine, benzo[b] furan and benzo[b] thiophene; and R is hydrogen or alkyl having 1 to 3 carbons.

The compounds of the formula (A), their preparation and their utility as an analgesic and antiinflammatory agents are fully described herein and in U.S. Pat. No. 4,556,672.

5-Fluoro-6-chlorooxindole has been previously prepared by Kadin, U.S. Pat. No. 4,556,672, via 3-chloro-4-fluoro-aniline which was reacted with chloroacetyl chloride to produce N-(2-chloroacetyl)-3-chloro-4-fluoroaniline, which in turn was cyclized in the presence of a strong alkali metal halide (Lewis Acid, e.g., aluminum chloride) to produce 5-fluoro-6-chlorooxindole.

Similar types of reactions, as illustrated in Scheme 2, using hydrogen fluoride-pyridine to rearrange an aromatic hydroxylamine is well-documented in the literature: Fidler et al., J. Org. Chem., 26, 4014 (1961), Patrick al. J. Org. Chem., 39, 1758 (1974). Incorporating a nitrile in the reaction to obtain the desired compound (III) from (IV) is novel and not anticipated by the literature. The desired compound (III) is not obtained, in the absence of an alkyl or aryl nitrile, when (IV) is reacted with hydrogen fluoride-pyridine or anhydrous hydrogen fluoride alone.

This invention also relates to the novel compounds (I) and (II) having the formulas

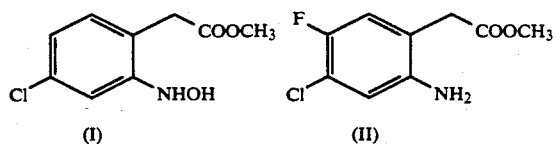

which are intermediates formed in the process of this invention and which therefore are useful for the production of the compound with formula (III).

SUMMARY OF THE INVENTION

We have now found that 5-fluoro-6-chlorooxindole (III) can be synthesized by either of two new processes, Method A or Method B, which affords a much higher yield of compound III) than the process cited in U.S. Pat. No. 4,556,672.

Method A comprises the steps of:

(a) rearranging methyl 2-(2-hydroxylamine-4-chlorophenyl)acetate (I) with a hydrogen fluoride source (e.g., anhydrous hydrogen fluoride or hydrogen fluoride-pyridine) to produce methyl (2-amino-4-chloro-5-fluorophenyl)acetate (II); and (b) cyclizing (II) with an acid in either an aqueous or organic cosolvent to produce the compound, 5-fluoro-6-chlorooxindole (III).

Method B comprises rearranging 5-chloro-1-hydroxy-oxindole (IV) with a hydrogen fluoride source (e.g., hydrogen fluoride-pyridine), in the presence of an alkyl or aryl nitrile to produce 5-fluoro-6-chloro-oxindole (III).

Method A is shown in Scheme i and Method B in Scheme 2.

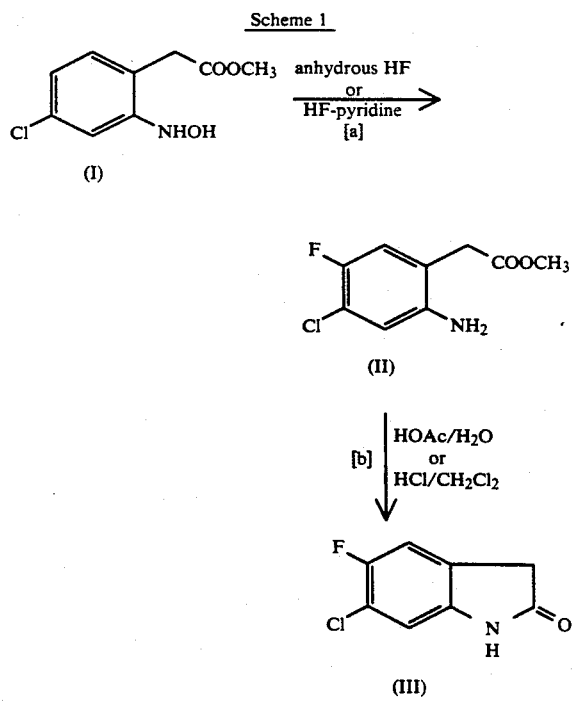

Method A

Scheme 2

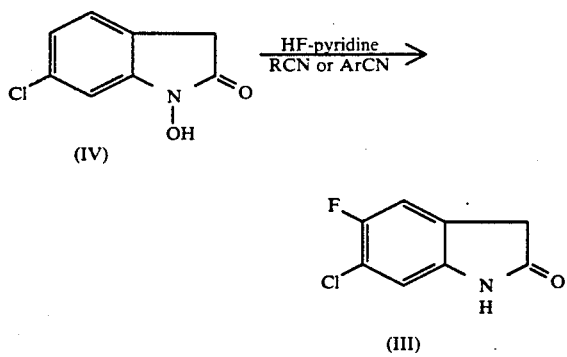

Method B

The present invention is also directed to compound of the formula

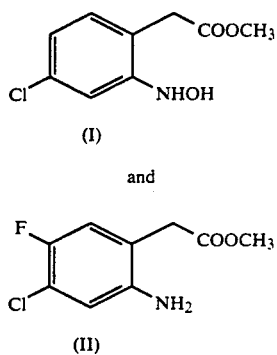

which are particularly vaulable intermediates in the preparation of the compounds of the formula (III).

DETAILED DESCRIPTION OF THE INVENTION

The overall processes of this invention are shown in Scheme 1 and Scheme 2.

The starting compound (I) in Scheme 1 is readily prepared from methyl 2-(2-nitro-4-chlorophenyl)acetate, 5% palladium on carbon, sodium hypophosphite and water, pursuant to the reactions described by Johnstone, et al., Tetrahedron 34, 213, (1978). In step [a] compound (I) is reacted with either hydrogen fluoride-pyridine or anhydrous hydrogen fluoride. In the case of hydrogen fluoride-pyridine, compound (I) is dissolved in a minimum amount of pyridine and added to an icebath cooled solution of the hydrogen fluoride-pyridine. After the addition, the temperature of the reaction is raised to 25° C. to 50° C. and the two reagents are allowed to react for one hour. The reaction mixture is cooled to room temperature and the pH of the mixture adjusted to 7 using a solution of weak base, preferably sodium carbonate. In the case of anhydrous hydrogen fluoride, compound (I) is cooled to −78° C. in a reaction vessel, anhydrous hydrogen fluoride is condensed into the reaction vessel and the vessel is sealed. The reaction mixture is warmed to 25° C. to 50° C. and stirred for between 3 to 4 hours. The reaction vessel is opened and excess hydrogen fluoride is aspirated off. In either case rearrangement occurs to produce methyl (2-amino-4-chloro-5-fluorophenyl)acetate (II). Compound (II) can be purified by standard techniques well known to those skilled in the art. Alternatively, compound (II) can be used directly for the next reaction step.

Compound (III) is obtained by cyclizing (II) with an acid as shown in step [b] of Scheme 1. Compound (II) is dissolved in a mixture of an acid and a cosolvent, preferably the acid is glacial acetic acid in which instance the preferred cosolvent is water or the acid is hydrochloric acid in which instance the preferred cosolvent is methylene chloride. With acetic acid the ratio of the acid and cosolvent mixture ranges from 2:1 to pure acetic acid respectively, the preferred ratio being 6:1. With HCl, much less acid is required, preferably 1:4 3N HCl to $CH_2Cl_2$. Once compound (II) is dissolved, the reaction mixture is stirred at ambient temperature for from 6 to 7 hours to produce 5-fluoro-6-chlorooxindole (III). Compound (III) is readily purified by recrystallization from ethyl acetate to yield an off-white solid.

Alternatively, compound (III) can be obtained by the reaction shown in Scheme 2. The starting compound (IV) is readily prepared by the reaction of compound (I) with a catalytic amount of 50% sulfuric acid. After 18 hours, the reaction mixture is filtered and compound (IV) is obtained as a yellow solid.

Compound (III) can be obtained by reaction of compound (IV) with hydrogen fluoride-pyridine in the presence of an alkyl or aryl nitrile. Compound (IV) and hydrogen fluoride-pyridine are mixed with an alkyl or aryl nitrile, preferably methoxyacetonitrile, acetonitrile or 2-cyanopyridine, in a reaction vessel. The vessel is sealed and the reaction mixture temperature is raised to 25° C. to 50° C. and stirred for approximately between 12 to 24 hours, 18 hours is preferred. After isolation by conventional means well known to those skilled in the art, a tan solid is obtained.

The following examples serve to illustrate the invention and are not to be construed as limiting the scope of this invention to the embodiments so exemplified. Nuclear magnetic resonance spectra (NMR) were measured on a 300 MHz instrument and peak positions are expressed in parts per million (ppm). The peak shapes are denoted as follows: s, singlet; br, broad; d, doublet; t, triplet; q, quartet; m, multiplet. "J" denotes the splitting constant which is also expressed in ppm.

EXAMPLE 1

Methyl (4-chloro-2-N-hydroxyamino] phenyl)acetate (I)

Methyl (2-nitro-4-chlorophenyl)acetate (5.0 g, 21.7 mmol) was dissolved in 250 ml of tetrahydrofuran and 15 ml of dimethyl sulfoxide. To this was added 900 mg of 10% pd/C. A solution of 5.38 g of sodium hypophosphite in 18 ml of water was added dropwise over a 40 minute period. After stirring for 4 hours another 2.68 g of sodium hypophosphite (in 8 ml of water) was added over a 10 minute period. After stirring for one hour the reaction mixture was filtered through Celite and the filtrate diluted with 500 ml of $CH_2Cl_2$. The filtrate was washed with saturated aqueous $NaHCO_3$ then brine and dried with $Na_2SO_4$. The solvents were evaporated under reduced pressure leaving 5.16 g of a yellow oil (110% of theory). NMR (300 MHz, $CDCl_3$) 3.51 (2H, s), 3.69 (3H, s), 5.50 (1H, br s), 6.88 (1H, dd, J=1,8), 7.01 (1H, d, J=8), 7.34 (1H, d, J=1), 7.56 (1H, br s).

EXAMPLE 2

Methyl (2-amino-4-chloro-5-fluorophenyl)acetate (II), Hydrogen fluoride-pyridine method A polypropylene flask containing 57 ml of HF-pyridine was cooled in an ice bath. Hydroxylamine (I) (2.34 g, 10.9 mmol) was added portionwise over a 12 minute period as a solution in 2 ml of pyridine. After the addition was complete the ice bath was removed and the mixture was warmed to 35° C. for 1 hour. After cooling to room temperature the reaction mixture was cautiously added to a solution of 115 g of $Na_2CO_3$ in 290 ml of water. The pH of the solution was, adjusted to 7 by addition of more $Na_2CO_3$ then extracted with ethyl acetate (3×300 ml). The combined ethyl acetate extracts were washed with water (2×200 ml) then brine (200 ml) and dried with $MgSO_4$. Removal of the solvents yielded 2.18 g of a tan solid. NMR (300 MHz, DMSO-$d_6$) 3.57 (2H, s), 3.63 (3H, s), 5.11 (2H, br s), 6.79 (1H, d, J=8), 7.06 (1H, d, J=10).

EXAMPLE 3

Methyl (2-amino-4-chloro-5-fluorophenyl)acetate (II), Anydrous hydrogen fluoride method Hydroxylamine (I) (0.50 g, 2.32 mmol) and a magnetic stir bar were added to a 100 ml teflon vessel. Cooled to −78° C. and 25 ml of anhydrous HF was condensed into the vessel. The vessel was sealed and allowed to warm to 20° C. The mixture was stirred for 3.4 hours at which time the vessel was opened and the HF removed under aspirator vacuum. The residue was dissolved in 50 ml of $CH_2Cl_2$ and washed with saturated aq. $NaHCO_3$ and dried with $Na_3SC_4$. Filtration and removal of solvents under vacuum yielded 0.41 g of a brown oil. The NMR was identical to that prepared by the HF-pyridine method.

EXAMPLE 4

5-Fluoro-6-chlorooxindole (III) From (II)

A crude amount of (II) (2.18 g) was dissolved in 60 ml of 6:1 HOAc/$H_2O$ and stirred for 6.5 hours. The solvents were evaporated under vacuum giving 1.93 g of a tan solid. The crude oxindole was recrystallized from ethyl acetate producing 1.2 g of an off-white solid. NMR (300 MHz, DMSO-$d_6$), 3.50 (2H, s), 6.89 (1H, d, J=7), 7.32 (1H, d, J=8), 10.50 (1H, br, s).

EXAMPLE 5

5-Fluoro-6-chlorooxindole (III) From (IV)

In a polypropylene flask was placed 20 ml of HF-pyridine. Then 4 ml of 2-cyanopyridine was added followed by 2.0 g (10.9 mmol) of (IV). The flask was sealed and heated to 45° C. for 18 hours. The reaction mixture was poured into 160 ml of water and extracted with ethyl acetate (3×200 ml). The combined ethyl acetate extracts were washed with 5% HCl (3×100 ml) and dried with $MgSC_4$. Filtration and evaporation of the solvents left 3.39 9 of a waxy brown solid that still contained 2-cyanopyridine. Trituration of this solid with isopropyl ether removed the 2-cyanopyridine leaving 1,80 g of a tan solid. The NMR of this material was identical to that obtained in Example 4.

PREPARATION 1

5-Chloro-1-hydroxyoxindole (IV)

The hydroxylamine (I) (200 mg, 0.92 mmol) was dissolved in 10 ml of ethanol. Then 8 drops of 50% $H_2SO_4$ was added. After 10 minutes a cream colored solid began to precipitate. The mixture was stirred at room temperature for 18 hours. The reaction was diluted with ethyl acetate (100 ml) washed with sat. aq. $NaHCO_3$ and dried with $Na_2SC_4$. After filtration, the solvents were evaporated under reduced pressure yielding 111 mg of a yellow solid. mp 202-208° C. NMR (300 MHz, DMSO-$d_6$) 3.58 (2H, s), 6.95 (1H, d, J=1), 7.06 (1H, dd, J=1,8), 7.26 (1H, d, J=8), 10.9 (1H, br, s).

I claim:

1. A process for the preparation of a compound of the formula

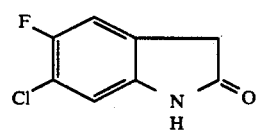

(III)

which comprises of rearranging a compound of the formula

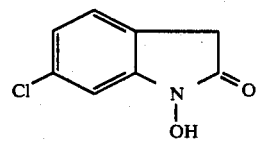

(IV)

with a hydrogen fluoride source in the presence of an alkyl or aryl nitrile to produce compound (III).

2. The process of claim 1 wherein the hydrogen fluoride source is hydrogen fluoride-pyridine.

3. The process of claim 1 which uses an alkyl nitrile and said alkyl nitrile is methoxyacetonitrile or acetonitrile.

4. The process of claim 1 which uses an aryl nitrile and said aryl nitrile is 2-cyanopyridine.

5. The process of claim 1 wherein the temperature of the reaction is controlled to from about 25.20 C. to 50° C.

* * * * *